US00PP34345P2

(12) United States Plant Patent
Hofmann

(10) Patent No.: US PP34,345 P2
(45) Date of Patent: Jun. 14, 2022

(54) ***LIMONIUM* PLANT NAMED 'INLIMPURPA'**

(50) Latin Name: *Limonium perezii*
Varietal Denomination: INLIMPURPA

(71) Applicant: Silvia Hofmann, Mainz (DE)

(72) Inventor: Silvia Hofmann, Mainz (DE)

(73) Assignee: InnovaPlant Zierpflanzen GmbH & Co. KG, Gensingen (DE)

( * ) Notice: Subject to any disclaimer, the term of this patent is extended or adjusted under 35 U.S.C. 154(b) by 10 days.

(21) Appl. No.: 17/372,310

(22) Filed: Jul. 9, 2021

(51) Int. Cl.
*A01H 5/02* (2018.01)
*A01H 6/00* (2018.01)

(52) U.S. Cl.
USPC ..... Plt./358

(58) Field of Classification Search
USPC ..... Plt./263.1, 358
See application file for complete search history.

*Primary Examiner* — Karen M Redden
(74) *Attorney, Agent, or Firm* — C. Anne Whealy

(57) ABSTRACT

A new and distinct cultivar of *Limonium* plant named 'INLIMPURPA', characterized by its relatively compact, upright and uniformly mounded plant habit; early and freely flowering habit; long flowering period; relatively large inflorescences with upright flowers with white-colored petals and purplish blue-colored sepals; and good garden performance.

2 Drawing Sheets

Figure 1:
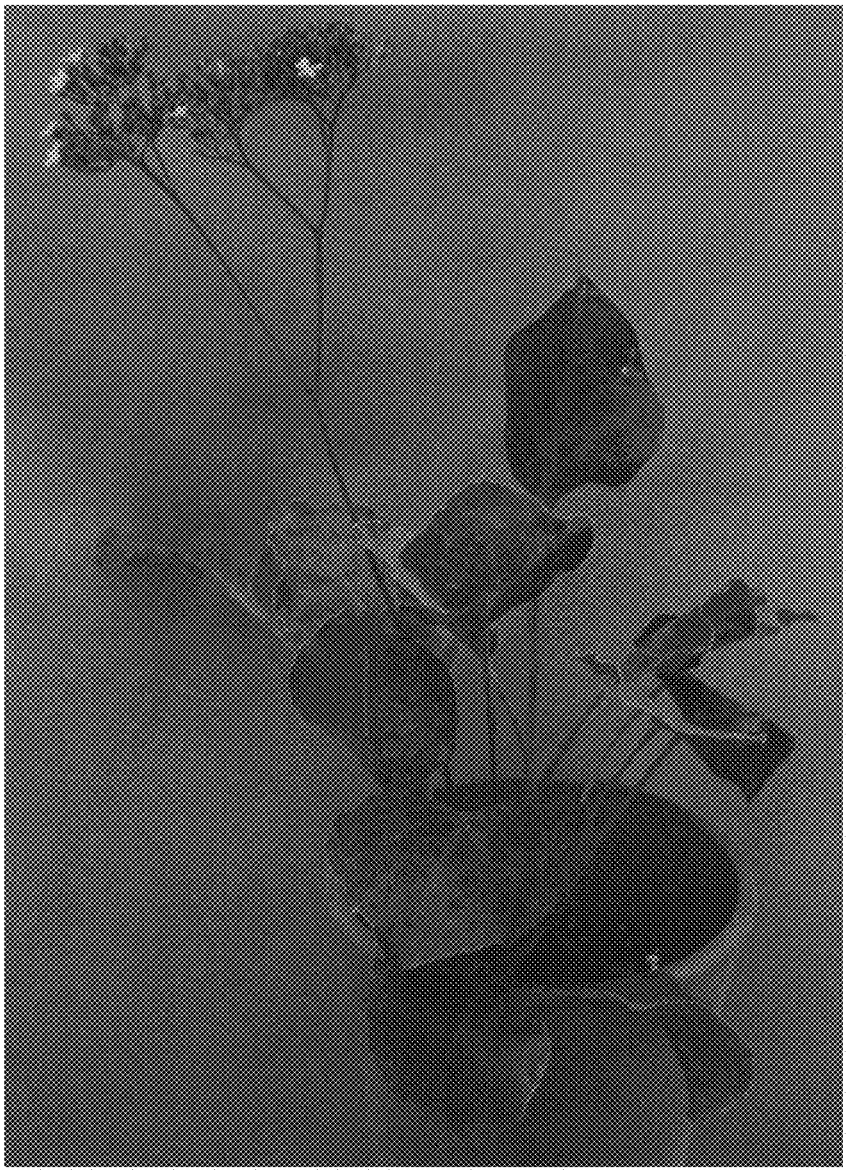

Botanical designation: *Limonium perezii.*
Cultivar denomination: 'INLIMPURPA'.

BACKGROUND OF THE INVENTION

The present invention relates to a new and distinct cultivar of *Limonium* plant, botanically known as *Limonium perezii*, commercially used as a potted *Limonium*, and hereinafter referred to by the name 'INLIMPURPA'.

The new *Limonium* plant is a product of a planned breeding program in Heidesheim and Gensingen, Germany. The objective of the breeding program is to create new pot-type *Limonium* plants with large inflorescences, attractive flower coloration and long flowering period.

The new *Limonium* plant originated from an open-pollination in Heidesheim, Germany in June, 2014 of an unnamed selection of *Limonium perezii*, not patented, as the female, or seed, parent with an unknown selection of *Limonium perezii* as the male, or seed, parent. The new *Limonium* plant was discovered and selected by the Inventor as a single flowering plant from within the progeny of the stated open-pollination grown in a controlled greenhouse environment in Heidesheim, Germany in August, 2014.

Asexual reproduction of the new *Limonium* plant by vegetative cuttings in a controlled environment in Gensingen, Germany since August, 2014 has shown that the unique features of this new *Limonium* plant are stable and reproduced true to type in successive generations.

SUMMARY OF THE INVENTION

Plants of the new *Limonium* have not been observed under all possible combinations of environmental conditions and cultural practices. The phenotype may vary somewhat with variations in environment such as temperature and light intensity without, however, any variance in genotype.

The following traits have been repeatedly observed and are determined to be the unique characteristics of 'INLIMPURPA'. These characteristics in combination distinguish 'INLIMPURPA' as anew and distinct *Limonium* plant:

1. Relatively compact, upright and uniformly mounded plant habit.
2. Early and freely flowering habit.
3. Long flowering period.
4. Relatively large inflorescences with upright flowers with white-colored petals and purplish blue-colored sepals.
5. Good garden performance.

Plants of the new *Limonium* can be compared to plants of the female parent selection. Plants of the new *Limonium* differ primarily from plants of the female parent selection in inflorescence size as plants of the new *Limonium* have larger inflorescences than plants of the female parent selection. In addition, plants of the new *Limonium* have larger leaves than plants of the female parent selection.

Plants of the new *Limonium* can be compared to plants of *Limonium perezii* 'Blue Compact', not patented. In side-by-side comparisons, plants of the new *Limonium* differed primarily from plants of 'Blue Compact' in the following characteristics:

1. Plants of the new *Limonium* are more vigorous than plants of 'Blue Compact'.
2. Plants of the new *Limonium* have larger inflorescences than plants of 'Blue Compact'.
3. Plants of the new *Limonium* flower for a longer period of time than plants of 'Blue Compact'.

BRIEF DESCRIPTION OF THE PHOTOGRAPHS

The accompanying colored photographs illustrate the overall appearance of the new *Limonium* plant showing the colors as true as it is reasonably possible to obtain in colored reproductions of this type. Colors in the photographs may differ slightly from the color values cited in the detailed botanical description which accurately describe the colors of the new *Limonium* plant.

The photograph on the first sheet (FIG. 1) is a side perspective view of a typical flowering plant of 'INLIMPURPA' grown in a container.

Figure 2:
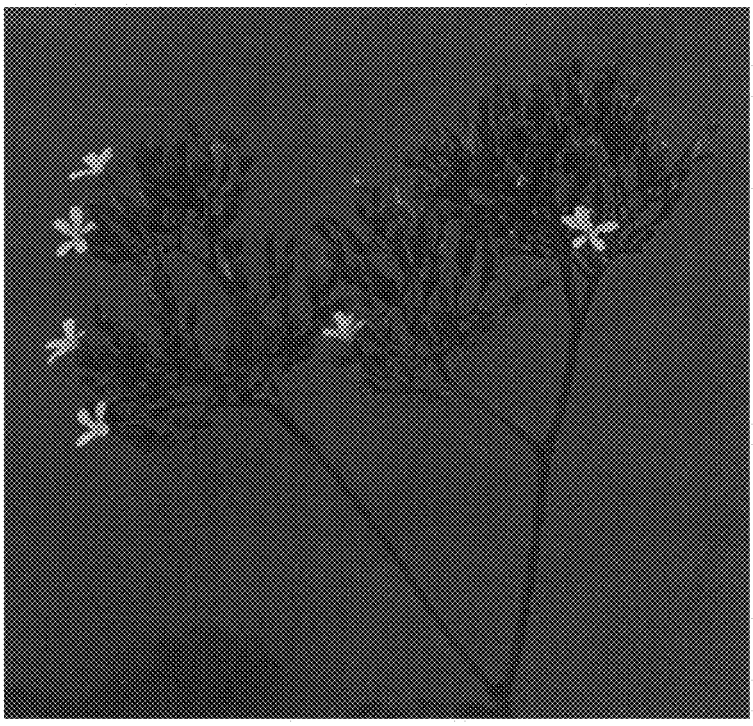

The photograph on the second sheet (FIG. 2) is a close-up view of a typical flowering plant of 'INLIMPURPA'.

DETAILED BOTANICAL DESCRIPTION

The aforementioned photographs and following observations and measurements describe plants grown during the spring in 10.8-cm containers in a glass-covered greenhouse in Loudon, N.H. and under cultural practices typical of commercial *Limonium* production. During the production of the plants, average daily temperatures were 21° C. Plants were ten weeks from planting when the photographs and description were taken. In the following description, color references are made to The Royal Horticultural Society Colour Chart, 2015 Edition, except where general terms of ordinary dictionary significance are used. Measurements were taken on individual plants.

Botanical classification: *Limonium perezii* 'INLIMPURPA'.

Parentage:

*Female, or seed, parent.*—Unnamed selection of *Limonium perezii*, not patented.

*Male, or pollen, parent.*—Unknown selection of *Limonium perezii*, not patented.

Propagation:

*Type.*—By in vitro meristem cuttings.

*Time to initiate roots, summer.*—About five to seven days at temperatures ranging from 21° C. to 27° C.

*Time to initiate roots, winter.*—About seven to ten days at temperatures ranging from 18° C. to 21° C.

*Time to produce a rooted young plant, summer.*—About three to four weeks at temperatures ranging from 21° C. to 27° C.

*Time to produce a rooted young plant, winter.*—About four to five weeks at temperatures ranging from 16° C. to 18° C.

*Root description.*—Fine, fibrous; typically white in color, actual color of the roots is dependent on substrate composition, water quality, fertilizer type and formulation, substrate temperature and physiological age of roots.

*Rooting habit.*—Moderately freely branching; medium density.

Plant description:

*Plant and growth habit.*—Herbaceous perennial grown as a potted and landscape plant; plants relatively compact, upright and uniformly mounded; leaves basal; freely flowering habit; numerous flowers arranged in compact dichasial cymes; vigorous growth habit and rapid growth rate.

*Plant height, soil level to top of foliar plane.*—About 20 cm.

*Plant height, soil level to top of inflorescences.*—About 30 cm.

*Plant diameter* (*spread*).—About 34 cm.

Leaf description:

*Arrangement.*—Basal rosette, simple.

*Length.*—About 8 cm.

*Width.*—About 7.5 cm.

*Shape.*—Roughly rhomboidal.

*Apex.*—Aristate.

*Base.*—Broadly obtuse to truncate.

*Margin.*—Entire to irregularly lobed, lobes shallow; ciliate; margins, undulate.

*Texture and luster, upper and lower surfaces.*—Smooth, glabrous; coriaceous; slightly glossy to matte.

*Venation pattern.*—Pinnate.

*Color.*—Developing and fully expanded leaves, upper surface: Close to 147A; venation, close to 147A. Developing and fully expanded leaves, lower surface: Darker green than 146A; venation, darker green than 146A.

*Petioles.*—Length: About 12 cm to 13 cm. Diameter: About 2.5 mm by 3 mm. Strength: Strong; flexible. Texture and luster, upper and lower surfaces: Slightly pubescent; slightly glossy. Color, upper and lower surfaces: Close to 146A; towards the base, close to 178A to 178B.

Flower description:

*Flower arrangement and habit.*—Single flowers arranged in relatively large and dense dichasial cymes; freely flowering habit with about 90 to 100 flowers developing per inflorescence; flowers face mostly upright.

*Fragrance.*—None detected.

*Natural flowering season.*—Long flowering period, plants flower from spring into the autumn; early flowering habit.

*Flower longevity on the plant.*—About five to seven days; persistent.

*inflorescence height, excluding peduncle.*—About 4 cm to 5.5 cm.

*Inflorescence diameter.*—About 4.2 cm to 5.5 cm.

*Flower diameter.*—About 6 mm.

*Flower depth* (*height*).—About 7 mm.

*Flower buds.*—Length: About 2 mm. Diameter: Less than 1 mm. Shape: Lanceolate, oblong. Color: Close to 147A.

*Petals.*—Quantity and arrangement: Five or occasionally six in a single whorl; petals are fused at the base. Length: About 1 cm. Width: About 1.5 mm. Shape: Oblanceolate. Apex: Broadly acute to obtuse or occasionally recuse. Margin: Entire. Texture, upper and lower surfaces: Smooth, glabrous; velvety. Color: When opening and fully opened, upper surface: Close to NN155A; venation, close to NN155A; color does not change with subsequent development. When opening and fully opened, lower surface: Close to NN155A, venation, close to NN155A; color does not change with subsequent development.

*Sepals.*—Quantity and arrangement: Five in a single whorl, totally fused; calyx tubular in shape. Length: About 6 mm. Width: About 1.5 mm. Shape: Lanceolate. Apex: Bluntly acute. Margin: Entire, fused. Texture and luster, upper and lower surfaces: Smooth, glabrous; satiny. Color, upper and lower surfaces: Close to 94B.

*Flower bracts.*—Quantity and arrangement: Two at the base of the flowers; opposite. Length: About 2.5 mm. Width: About 1 mm. Shape: Acicular. Apex: Acuminate. Margin: Entire. Texture and luster, upper and lower surfaces: Smooth, glabrous; slightly glossy. Color, upper surface: Close to 144A. Color, lower surface: Close to 147A.

*Peduncles.*—Length: About 26 cm. Diameter: About 3 mm. Aspect: Upright. Strength: Strong, flexible. Texture and luster: Smooth, glabrous; slightly glossy. Color: Close to 147A.

*Pedicels.*—Length: About 2 mm to 3 mm. Diameter: Less than 1 mm. Strength: Strong, flexible. Angle: About 45° from peduncle axis. Texture and luster: Smooth, glabrous; slightly glossy. Color: Close to 147A.

*Reproductive organs.*—Androecium: Stamen number: Five per flower. Filament length: About 3 mm. Filament color: Close to NN155A. Anther length: About 1 mm. Anther shape: Oblong. Anther color: Close to 1 1D. Amount of pollen: None observed. Gynoecium: Pistil number: One per flower. Pistil length: About 3.5 mm. Style length: About 3 mm. Style color: Close to 157D. Stigma shape: Capitate. Stigma color: Close to 11D. Ovary color: Close to 144A to 144B.

*Seeds and fruits.*—To date, seed and fruit development have not been observed on plants of the new *Limonium.*

Pathogen & pest resistance: To date, plants of the new *Limonium* have not been observed to be resistant to pathogens and pests common to *Limonium* plants.

Garden performance: Plants of the new *Limonium* have been observed to have good garden performance and to tolerate wind, rain and temperatures ranged from about 5° C. to about 35° C.

It is claimed:

1. A new and distinct *Limonium* plant named 'INLIMPURPA' as illustrated and described.

* * * * *